(12) United States Patent
Simpson et al.

(10) Patent No.: US 8,500,786 B2
(45) Date of Patent: *Aug. 6, 2013

(54) RADIOPAQUE MARKERS COMPRISING BINARY ALLOYS OF TITANIUM

(75) Inventors: John A. Simpson, Carlsbad, CA (US); John F. Boylan, Murrieta, CA (US)

(73) Assignee: Abbott Laboratories, Abbott Park, IL (US)

( * ) Notice: Subject to any disclaimer, the term of this patent is extended or adjusted under 35 U.S.C. 154(b) by 508 days.

This patent is subject to a terminal disclaimer.

(21) Appl. No.: 11/748,797

(22) Filed: May 15, 2007

(65) Prior Publication Data

US 2008/0288056 A1  Nov. 20, 2008

(51) Int. Cl.
*A61F 2/06* (2006.01)

(52) U.S. Cl.
USPC .......................... 623/1.11; 623/1.34

(58) Field of Classification Search
USPC ...... 606/108; 623/1.11, 1.15, 1.34; 228/196, 228/197, 119; 420/417; 428/656, 660, 661, 428/637; 148/669
See application file for complete search history.

(56) References Cited

U.S. PATENT DOCUMENTS

| | | | |
|---|---|---|---|
| 3,735,478 A * | 5/1973 | Porter et al. .................. 228/144 |
| 3,832,243 A * | 8/1974 | Donkersloot et al. ........ 148/402 |
| 4,039,244 A * | 8/1977 | Leachy .......................... 439/887 |
| 4,310,354 A | 1/1982 | Fountain et al. |
| 4,580,568 A | 4/1986 | Gianturco |
| 4,759,906 A | 7/1988 | Nenno et al. |
| 4,856,516 A | 8/1989 | Hillstead |
| 4,881,981 A | 11/1989 | Thoma et al. |
| 5,092,877 A | 3/1992 | Pinchuk |
| 5,292,331 A | 3/1994 | Boneau |
| 5,341,818 A | 8/1994 | Abrams et al. |
| 5,350,419 A | 9/1994 | Bendel et al. |
| 5,514,154 A | 5/1996 | Lau et al. |
| 5,628,787 A * | 5/1997 | Mayer .......................... 623/1.15 |
| 5,759,174 A | 6/1998 | Fischell et al. |
| 5,843,244 A | 12/1998 | Pelton et al. |
| 5,968,038 A * | 10/1999 | Djeu ............................... 606/16 |
| 6,106,642 A | 8/2000 | DiCarlo et al. |
| 6,168,570 B1 * | 1/2001 | Ferrera .......................... 600/585 |
| 6,174,329 B1 * | 1/2001 | Callol et al. .................. 623/1.34 |

(Continued)

FOREIGN PATENT DOCUMENTS

| | | |
|---|---|---|
| EP | 0239747 | 10/1987 |
| EP | 0873734 | 10/1998 |

(Continued)

OTHER PUBLICATIONS

T. Biggs et al., "Martensitic Transformations, Microstructure, and Mechanical Workability of TiPt", Metallurgical and Materials Transactions A; vol. 32A, No. 8; pp. 1881-1886.

(Continued)

*Primary Examiner* — Gary Jackson
*Assistant Examiner* — Jonathan Hollm
(74) *Attorney, Agent, or Firm* — Workman Nydegger; Jonathan Feuchtwang

(57) ABSTRACT

There is disclosed a radiopaque marker comprising a binary alloy of titanium and one binary element selected from platinum, palladium, rhodium, and gold. There is also disclosed various medical devices, such as stents, guidewires and embolic filters, that have the radiopaque marker attached thereto. Methods of attaching the radiopaque marker to the medical devices, such as by welding, are also disclosed.

31 Claims, 2 Drawing Sheets

U.S. PATENT DOCUMENTS

| | | | |
|---|---|---|---|
| 6,179,859 B1 | 1/2001 | Bates et al. | |
| 6,334,871 B1 * | 1/2002 | Dor et al. | 623/1.34 |
| 6,419,693 B1 | 7/2002 | Fariabi | |
| 6,497,671 B2 | 12/2002 | Ferrera et al. | |
| 6,503,272 B2 * | 1/2003 | Duerig et al. | 623/1.24 |
| 6,638,301 B1 | 10/2003 | Chandrasekaran et al. | |
| 6,706,053 B1 | 3/2004 | Boylan et al. | |
| 6,855,161 B2 * | 2/2005 | Boylan et al. | 623/1.19 |
| 2002/0082681 A1 | 6/2002 | Boylan et al. | |
| 2002/0198601 A1 | 12/2002 | Bales et al. | |
| 2003/0120181 A1 | 6/2003 | Toma et al. | |
| 2004/0068315 A1 * | 4/2004 | Chandrasekaran et al. | 623/1.15 |
| 2004/0106878 A1 * | 6/2004 | Skujins et al. | 600/585 |
| 2004/0236409 A1 | 11/2004 | Pelton et al. | |
| 2005/0038500 A1 * | 2/2005 | Boylan et al. | 623/1.18 |
| 2005/0060025 A1 * | 3/2005 | Mackiewicz et al. | 623/1.34 |
| 2006/0079953 A1 | 4/2006 | Gregorich et al. | |
| 2006/0276875 A1 * | 12/2006 | Stinson et al. | 623/1.15 |
| 2007/0042259 A1 * | 2/2007 | Fan et al. | 429/40 |
| 2008/0288056 A1 | 11/2008 | Simpson et al. | |
| 2009/0099645 A1 | 4/2009 | Simpson et al. | |

FOREIGN PATENT DOCUMENTS

| | | |
|---|---|---|
| EP | 1 212 991 A | 6/2002 |
| JP | 11050282 | 2/1999 |
| JP | 2002212664 | 7/2002 |
| WO | WO 02/05863 | 1/2002 |
| WO | WO2005032403 | 4/2005 |
| WO | WO2008141336 | 11/2006 |
| WO | WO2008033603 | 3/2008 |

OTHER PUBLICATIONS

T. Biggs et al., "The Effect of Nickel on the Martensitic-type Transformations of $Pt_3$ and TiPt," Journal de Physique IV; vol. 11, issue 8, pp. 493-498 [ESOMAT 2000: 5 European Symposium on Martensitic Transformations and Shape Memory Alloys, Como, Italy, Sep. 4-8, 2000].

International Search and Written Opinion based on PCT/US2008/063690, mailed Jul. 28, 2008.

U.S. Appl. No. 12/153,254, Sep. 2, 2009, OA.

U.S. Appl. No. 12/153,254, May 10, 2010, OA.

U.S. Appl. No. 12/153,254, Aug. 4, 2011, Office Action.

U.S. Appl. No. 12/153,254, Dec. 16, 2011, Office Action.

U.S. Appl. No. 12/153,254, Aug. 30, 2012, Office Action.

* cited by examiner

RADIOPAQUE MARKERS COMPRISING BINARY ALLOYS OF TITANIUM

The present disclosure relates to radiopaque markers comprising binary alloys of titanium. The present disclosure also relates to medical devices having the radiopaque markers attached thereto, such as stents, guidewires, embolic protection devices, or other components of a stent delivery system.

Stents are generally thin walled tubular-shaped devices composed of complex patterns of interconnecting struts which function to hold open a segment of a blood vessel or other body lumen such as a coronary artery. They also are suitable for supporting a dissected arterial lining or intimal flap that can occlude a vessel lumen.

Guidewires are used for advancing intraluminal devices to the desired location within a body lumen in angioplasty, stent delivery, atherectomy and other vascular procedures. A conventional guidewire usually comprises an elongated core member with one or more tapered sections near the distal end thereof and a flexible body such as a helical coil or a tubular body of polymeric material disposed about the distal portion of the core member. The flexible body may extend proximally to an intermediate portion of the guidewire.

Embolic protection devices serve to capture and remove the debris created by angioplasty, stent delivery, atherectomy and other vascular procedures. It prevents the debris from flowing downstream and blocking the artery. One type of embolic protection device is filter-based, which allows the blood in the artery to continue flowing while the filter traps the debris.

Traditional stent delivery systems comprise a guidewire, a stent-delivery catheter, a stent, and may include an embolic protection device. A stent is typically implanted using a catheter which is inserted at an easily accessible location and then advanced through the vasculature to the deployment site. The stent is initially maintained in a radially compressed or collapsed state to enable it to be maneuvered through the lumen. Once in position, the stent is deployed. In the case of self-expanding stents, deployment is achieved by the removal of a restraint, such as the retraction of a delivery sheath. In the case of balloon expandable stents, deployment is achieved by inflation of a dilatation balloon about which the stent is carried on a stent-delivery catheter.

Stents, guidewires, embolic protection devices, and other components in a stent delivery system can be constructed at least partially using a superelastic material, such as nickel-titanium alloys, also known as nitinol. An embolic filter made of nitinol is shown in, for example, U.S. Pat. No. 6,179,859 (Bates et al.), which is herein incorporated by reference. A guide wire made from nitinol is shown in, for example, U.S. Pat. No. 5,341,818 (Abrams), which is herein incorporated by reference.

In general, superelasticity implies that the material can undergo a large degree of reversible strain as compared to common steel. In a technical sense, the term "superelasticity" and sometimes "pseudoelasticity" refer to an isothermal transformation in nitinol. More specifically, it refers to stress inducing a martensitic phase from an austenitic phase at a temperature above the martensitic transformation temperature.

Nitinol alloys, for example, exhibit both superelasticity and the shape memory effect. The literature describes various processing techniques to enhance these valuable properties. These techniques include changing the relative amounts of nickel and titanium, alloying the nickel-titanium with other elements, heat treating the alloy, and mechanical processing of the alloy. Examples of such techniques include U.S. Pat. No. 4,310,354 (Fountain), which discloses processes for producing a shape memory nitinol alloy having a desired transition temperature; U.S. Pat. No. 6,106,642 (DiCarlo), which discloses a process for improving ductility of nitinol, U.S. Pat. No. 5,843,244 (Pelton), which discloses cold working and annealing a nitinol alloy to lower a transformation temperature; U.S. Publication No. US 2003/0120181A1, published Jun. 26, 2003, which discloses work-hardened pseudoelastic guide wires; U.S. Pat. No. 4,881,981 (Thoma et al.), which discloses a process for adjusting the physical and mechanical properties of a shape memory alloy member by increasing the internal stress level of the alloy by cold work and heat treatment; and U.S. Pat. No. 6,706,053 (Boylan et al.) which teaches adding a ternary element to a nickel-titanium alloy to enhance engineering properties suitable for an embolic filter.

Superelastic characteristics generally allow the metal stent to be deformed by collapsing the stent and creating stress which causes the superelastic material to reversibly change to the martensitic phase. Once the stress is released, the martensitic phase reverses back to austenitic phase. This release of stress such that the stent returns towards its original undeformed shape through isothermal transformation back to the austenitic phase is described as "self-expanding."

Self-expanding, nickel-titanium stents have long been useful and valuable to the medical field. But a distinct disadvantage with self-expanding nickel-titanium stents is the fact that they are not sufficiently radiopaque.

An intracorporeal device and its delivery system should be radiopaque or fluoroscopically visible. For instance, accurate stent placement requires real time visualization to allow the physician to track the delivery catheter through the patients vasculature and precisely place the stent at the site of a lesion. This is typically accomplished by fluoroscopy or similar x-ray visualization procedures. For a device to be fluoroscopically visible it must be more absorptive of x-rays than the surrounding tissue. Good radiopacity is therefore a useful feature for self-expanding nickel-titanium stents to have.

Radiopacity can be improved by increasing the strut thickness of the nickel-titanium stent. But increasing strut thickness detrimentally affects the flexibility of the stent, which is a quality necessary for ease of delivery. Another complication is that radiopacity and radial force vary with strut thickness.

Radiopacity can also be improved through coating processes such as sputtering, plating, or co-drawing gold or similar heavy metals onto the stent. These processes, however, create complications such as material compatibility, galvanic corrosion, high manufacturing cost, coating adhesion or delamination, biocompatibility, loss of coating integrity following collapse and deployment of the stent Further, they may retard the dimensional recovery of a self expanding stent during deployment and potentially increase the delivery profile of the crimped stent.

In addition, radiopacity can be improved by alloy addition, such as by alloying nickel-titanium with a ternary element. This approach, however, typically requires one to strike a balance between achieving sufficient degree of radiopacity and maintaining the desirable superelastic engineering properties typical of a binary nickel-titanium.

One method for increasing fluoroscopic visibility is the physical attachment of radiopaque markers to the intracorporeal device and its delivery system. The attachment can be accomplished by various techniques, such as welding. It is well known, however, that nitinol can be difficult to weld to another metal or alloy since the nickel or titanium in nitinol will typically combine with one or more elements in the other material to product intermetallic compounds. These intermetallic compounds usually cause cracking during cooling and have an adverse impact on weld joint ductility.

What is needed therefore is a radiopaque marker that is compatible with materials in the medical devices mentioned above and their delivery systems. Such a marker should be sufficiently radiopaque to be readily visible using fluoroscopy procedures, and also can be readily attached to the medical device and its delivery system.

SUMMARY OF THE INVENTION

The present disclosure is generally directed to a radiopaque marker comprising a binary alloy of titanium and one binary element chosen from platinum, palladium, rhodium, and gold. The disclosure is also directed to a medical device, such as a stent, guidewire, or embolic filter device, having the radiopaque marker attached thereto. In one embodiment, the radiopaque marker is attached to the medical device by welding, such as fusion welding, wherein one or both components is melted.

Another aspect of the present disclosure is directed to a stent delivery system comprising an expandable or self-expanding section, and a radiopaque marker comprising a binary alloy of titanium and one element chosen from platinum, palladium, rhodium, and gold integrally attached to the expandable or self-expanding section.

There is also disclosed a method of fabricating a medical device comprising a radiopaque marker. In one embodiment, the method comprises welding to an expandable or self-expanding section of a medical device, such as by fusion welding, a radiopaque marker described herein.

Various embodiments of the present disclosure can be used in medical devices used in arteries, veins, and other body vessels. It is to be understood that the present invention is not limited by the embodiments described herein. Other features and advantages of the present invention will become more apparent from the following detailed description of the invention when taken alone or in conjunction with the accompanying exemplary drawing.

DETAILED DESCRIPTION OF THE INVENTION

Figure 1:
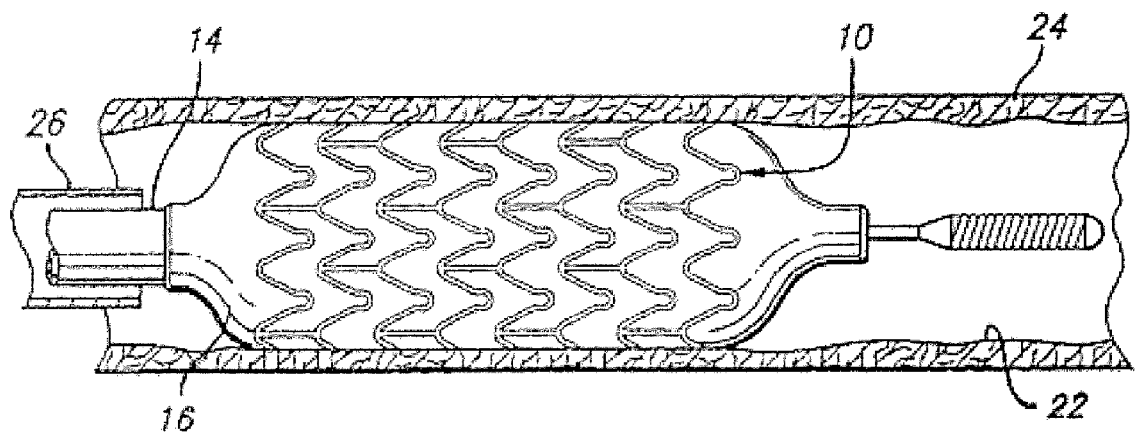
FIG. 1 depicts a stent expanded within the artery, so that the stent makes intimate contact with the arterial wall.

The present disclosure is generally directed to titanium containing binary alloys that can be used in a wide variety of non-medical and medical applications. While the following discussion exemplifies medical device applications, the disclosure is not so limited. Rather, it is appreciated that the disclosure broadly encompasses any application that could utilize the radiopaque and weldable characteristics of the resulting alloy. Therefore, while the invention described below is directed to the binary, radiopaque alloy attached to a medical device, such as a stent, it is understood that the present invention is applicable to other medical devices usable in a body lumen or outside a body lumen, or more generally to non-medical devices.

Commercially available materials used in medical devices typically comprise superelastic alloys. While such alloys have been extremely successful in applications that exploit their self-expanding properties, such as stents and embolic filtering devices, they typically have poor radiopacity because they comprise low amounts of radiopaque elements.

The present invention improves on existing medical devices by utilizing the heretofore unappreciated properties of certain binary alloys of titanium and an element selected from platinum, palladium, rhodium, and gold as a marker on such devices. For example, medical devices, such as stents having the inventive alloys attached thereto, are sufficiently radiopaque to be readily visualized under fluoroscopy during a stent placement procedure, yet are not so radiopaque as to interfere with the visualization of surrounding body tissue or stent lumen. In addition, since the stent comprises a radiopaque material welded thereto, the inventive stent overcomes the drawbacks associated with traditional composite or plated stents, such as retarded deployment and separation of the radiopaque layer.

The stent of the present invention can have virtually any configuration that is compatible with the body lumen in which it is implanted. Typically stents are composed of an intricate geometric pattern of cylindrical rings and connecting links. Non-limiting examples of intravascular stents can be found in U.S. Pat. No. 5,292,331 (Boneau); U.S. Pat. No. 4,580,568 (Gianturco); U.S. Pat. No. 4,856,516 (Hilistead); U.S. Pat. No. 5,092,877 (Pinchuk); and U.S. Pat. No. 5,514,154 (Lau et al.), which are incorporated herein by reference in their entirety.

These elements are commonly referred to as struts. Generally, the struts are arranged in patterns which are designed to contact the lumen walls of a vessel and to maintain patency of the vessel thereby. A myriad of strut patterns are known in the art for achieving particular design goals. A few of the more important design characteristics of stents are radial or hoop strength, expansion ratio, coverage area and longitudinal flexibility. One strut pattern may be selected over another in an effort to optimize those parameters that are of importance for a particular application.

Regardless of the specific application, with most lesion treatment procedures, the treated artery suffers a degree of trauma and in a certain percentage of cases may abruptly collapse or may slowly narrow over a period of time due to neointimal hyperplasia which is referred to as restenosis. To prevent either of these conditions, the treated artery is often fitted with a prosthetic device, such as the stent 10, shown in FIG. 1 of the present invention.

The stent provides radial support for the treated vessel and thereby prevents collapse of the vessel 24 and further provides scaffolding to prevent plaque prolapse within the lumen. The stent may also be used to repair an arterial dissection, or an intimal flap, both of which are commonly found in the coronary arteries, peripheral arteries and other vessels. In order to perform its function, the stent must be accurately placed across the lesion site.

Therefore, it is desirable that the stent be sufficiently radiopaque so that the physician can visually locate the stent under fluoroscopy during the implantation procedure. However, it is equally important that the stent not be too radiopaque. If the stent is overly radiopaque then the physician's view of the lumen is compromised. This makes assessment of subsequent restenosis difficult. In cases where the balloon markers are very close to the stent, the stent can blend in with the overly radiopaque markers. Without precise visualization of the stent ends, accurate placement of the stent in a lesion, particularly in the case of an ostial lesion, can be compromised.

In a typical stent placement procedure, a guiding catheter is percutaneously introduced into the cardiovascular system of a patient through the femoral arteries by means of a conventional technique, such as a Seldinger technique, and advanced within a patients vascular system until the distal end of the guiding catheter is positioned at a point proximal to the lesion site. A guide wire and the stent-delivery catheter of the rapid exchange type are introduced through the guiding catheter with the guide wire sliding within the stent-delivery catheter. The guide wire is first advanced out of the guiding catheter into the arterial vessel and is directed across the arterial lesion. The stent-delivery catheter is subsequently advanced over the previously advanced guide wire until the stent is properly positioned across the lesion.

Referring again to FIG. 1, once in position, the dilatation balloon 16 is inflated to a predetermined size to radially expand the stent 10 against the inside of the artery wall and thereby implant the stent within the lumen 22 of the artery. The balloon is then deflated to a small profile so that the stent-delivery catheter may be withdrawn from the patient's vasculature and blood flow is resumed through the artery.

Since the stent 10 is formed from an elongated tubular member, the rings and links of the stent are relatively flat in transverse cross-section, thus after implantation into the artery 24, minimal interference with blood flow occurs.

Eventually the stent becomes covered with endothelial cell growth which further minimizes blood flow interference. As should be appreciated by those skilled in the art, while the above-described procedure is typical, it is not the only method used in placing stents.

Typically, the stent 10 is laser cut from a solid tube. Thus, the stent does not possess discrete individual components. However, for the purposes of description it is beneficial to refer to the exemplary embodiment of the stent as being composed of cylindrical rings and connecting links.

in order to achieve the desirable radiopaque properties, the present invention uses binary alloy markers welded onto the medical devices that assist the physician to visually locate the stent under fluoroscopy during any invasive procedure.

The Inventors have discovered that binary alloys of titanium are metallurgically compatible when welded to either binary nitinol or a ternary nitinol that contains minor amounts of ternary elements, such as up to 10 atomic percent, including the range of 7-8 atomic percent. In addition to the improved weldable properties associated with metallurgical compatibility, the enhanced radiopaque properties make the inventive alloy ideal as a weldable radiopaque marker for medical devices.

The compatibility of the titanium based binary alloys described herein lies in the fact that the binary elements described are direct substitutes for nickel within the nitinol crystal structure. Furthermore, such replacement can occur at any amount up to complete substitution. Evidence of this phenomenon is show in the phase diagrams for some known binary alloys, such as nickel-platinum, nickel-titanium, titanium-platinum, and other binary alloys.

For example, as shown in "Binary Alloy Phase Diagrams", American Society for Metals, 1986, which is incorporated by reference herein, the phase diagram for the binary nickel-platinum alloy reveals that mixtures of nickel and platinum will combine to form one solid solution upon solidification, regardless of the composition. This is because nickel and platinum atoms are sufficiently alike, such as in atomic radius and electronegativity, that there are no mixture ratios that correspond to intermediate compounds or phases.

In contrast, the phase diagram for the binary nickel-titanium alloy reveals a variety of phases and compounds, depending on the particular composition. This is because Ni and Ti atoms are not nearly as similar as nickel and platinum in atomic radius and electronegativity. One type of nitinol is a binary alloy of nickel and titanium which contains approximately 50% nickel and 50% titanium, and is unusual in that it possesses a reversible martensitic transformation temperature that is responsible for shape memory and superelastic behavior. In other words, above the martensitic transformation temperature without external load, binary nitinol exists in the austenitic state. Its overall structure is the B2 crystal lattice, the so called cesium chloride structure. In this structure each Ni atom is positioned such that all of its nearest neighbors are titanium atoms and vice versa.

The relatively simple crystal structure and a large number of slip systems allow binary nitinol to be easily deformed and ductile. Depending upon the composition of the alloy, from about 45% nickel upward to about 55% nickel, the transformation temperature boundary of this phase may be lowered.

Similarly, titanium-platinum binary alloys at near equiatomic compositions exist in a phase which has lattice structure similar to nitinol at above its martensitic transformation temperature. At room temperature, the near equiatomic phase is relatively soft and workable. For instance, Ti50Pt50 has a hardness of about 250 HV and is cold rollable to approximately 50% reduction in thickness without edge cracking. The phase boundary is at about 45 and 56% of titanium, corresponding to compositions varying from Ti45Pt55 to Ti56Pt44.

As previously stated, nickel and platinum atoms are sufficiently alike in atomic radius and electronegativity such that the nickel-platinum alloy comprises a solid solution without intermediate phases or compounds. Other metals that are able to form solid solution with Ni without intermediate phases or compounds include palladium, rhodium, and gold. Furthermore, platinum, palladium, rhodium, and gold are significantly more radiopaque than nickel and can be used in making radiopaque alloy markers according to the present invention.

The characteristics of nickel-platinum, nickel-titanium, titanium-platinum binary alloys discussed above indicate that, as long as titanium is approximately 50%, platinum may replace nickel in a ternary nickel-titanium-platinum alloy up to full substitution and the resulting lattice structure will maintain the same B2 structure. Furthermore, any such ternary composition, designated as Ti50[Ni, Pt]50, will behave in a ductile manner like the binary Ti50Ni50 and Ti50Pt50 phases.

In one embodiment, a binary Ti50Ni50 alloy is autogenously welded to a Ti50Pt50 alloy marker. As the molten weld pool conforms to the stoichiometry of Ti50[Ni, Pt]50, the resulting weld is essentially free of undesirable intermetallic compounds Thus the welded product retains good ductility.

Similarly, the Ti50Pt50 alloy marker can form a weld free of intermetallic compounds to any ternary titanium-nickel-platinum alloy that has a composition at or near Ti50[Ni, Pt]50. For example, in another embodiment, the radiopaque marker described herein may be welded to a ternary titanium nickel alloy comprising from 7-8 atomic % of platinum, such as Ti50Ni42.5Pt7.5.

By contrast, if a pure platinum marker is welded to a binary nickel-titanium alloy and both components experienced some degree of melting, then the bulk composition of the molten weld pool would generally not maintain Ti50[Ni, Pt]50 stoichiometry. The solidified weld zone may contain a variety of intermetallic compositions, most of which do not have a lattice structure similar to Ni50Ti50 or Ti50Pt50. Such a weld could have poor ductility and may tend to crack.

Figure 2:
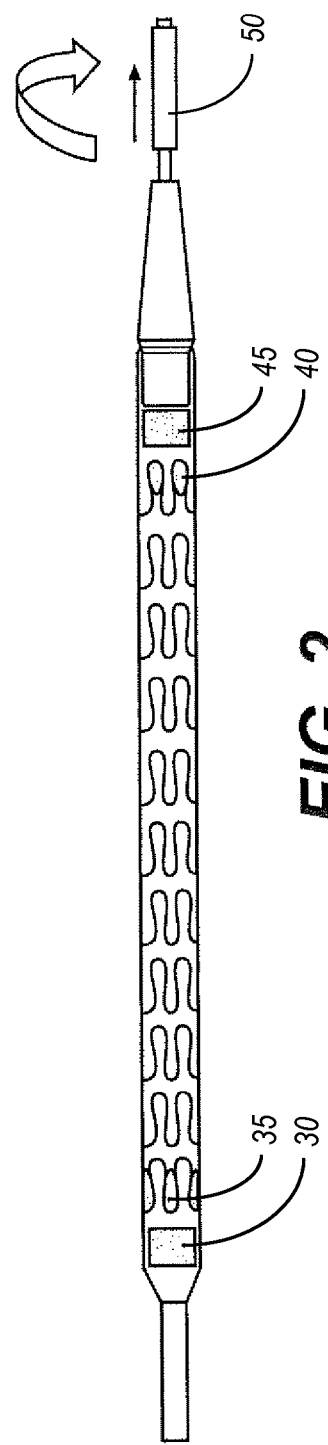
FIG. 2 depicts a stent according to one embodiment of the present disclosure showing the position of radiopaque markers attached thereto.

FIG. 2 illustrates a stent showing the inventive radiopaque markers attached thereto. In this non-limiting embodiment, the inventive alloy may be used as proximal (30) and distal (45) markers that are welded, such as by fusion welding, to both ends of the stent. In addition or in the alternative, small, teardrop-shaped markers, which have been laser cut from the inventive binary alloy or have been formed by other means, can be welded as stent markers (35, 40) to either end of the stent.

As previously stated, the inventive alloys are metallurgically compatible with the underlying nitinol substrate (whether binary or ternary), thus allowing the radiopaque markers to be fusion welded in place. As a result, the weld joint of a medical device made according to the present invention avoids the brittle intermetallic compounds and subsequent potential cracking typically associated with thermal or mechanical cycling of traditional markers on medical devices.

One embodiment of the present invention is a radiopaque marker that comprises a binary titanium-platinum alloy. The atomic percent of titanium in the alloy may range from 45 to 56, such as from 49 to 51, with the balance comprising platinum.

In another embodiment, the binary alloy comprises an equiatomic amount of titanium and platinum, e.g., Ti50Pt50. The radiopaque marker is integrally attached to a superelastic alloy, such as by a weld between the radiopaque marker and a superelastic alloy.

In other embodiments of the present invention, the superelastic alloy comprises a binary nickel-titanium alloy, or a ternary alloy of nickel and titanium, and comprising at least one ternary element chosen from platinum, palladium, gold and rhodium.

The superelastic alloy according to other embodiments can comprise a ternary alloy of nickel, titanium, and platinum, and may be expandable or self-expandable.

In another embodiment of the present invention, the ternary alloy comprises 49 to 51 atomic percent titanium, 7 to 8 atomic percent platinum, with the remainder comprising nickel.

The present disclosure is also directed to a medical device that comprises a radiopaque marker having a binary titanium-platinum alloy as described above. The medical device may include a stent, a guidewire, or an embolic protection device. The radiopaque marker can be integrally attached to or welded to the stent, the guidewire, or the embolic protection device.

One non-limiting embodiment of the present disclosure is directed to a stent delivery system comprising an expandable or self-expanding section, and a radiopaque marker integrally attached to the expandable or self-expanding section. The radiopaque marker comprises the previously described binary alloy of titanium, which includes one binary element selected from platinum, palladium, rhodium, and gold. The titanium may be present in the radiopaque marker in an amount ranging from 45 to 56 atomic percent, such as from 49 to 51 atomic percent, or even about 50 atomic percent, with the balance comprising a binary element of platinum, palladium, rhodium, or gold.

In the above mentioned stent delivery system the radiopaque marker can be integrally attached to the expandable or self-expanding section by a weld. The expandable or self-expanding section may comprise a binary nickel-titanium alloy or a ternary alloy of nickel and titanium. The ternary alloy comprises at least one ternary element chosen from platinum, palladium, gold and rhodium.

The above-mentioned stent delivery system may further comprise a guidewire. In one embodiment, the guidewire may also have the radiopaque marker 50 attached thereto.

The invention further provides a method of fabricating a medical device comprising a radiopaque marker. The method comprises welding to an expandable or self-expanding section, a radiopaque marker comprising a binary alloy of titanium and one binary element selected from platinum, palladium, rhodium, and gold.

As stated, fluoroscopy, utilizing x-rays, is by far the most popular imaging method used to visualize medical devices, such as stents. This is the case both during an intervention (delivering a stent) and afterwards in a more diagnostic mode. The present invention stent also is visible under magnetic resonance imaging (MRI), which works completely differently from that of fluoroscopy. Thus, a medical device comprising the inventive markers will show up in an MRI image in a fundamentally different way than under x-ray, primarily as an imaging artifact associated with the magnetic susceptibility and electrical conductivity of the inventive markers.

Any metal that has a magnetic susceptibility different from that of tissue will generate a susceptibility artifact. The magnitude of the artifact depends on how much the susceptibility differs from that of tissue. These artifacts usually are signal voids or dark spots on the image. Electrically conductive metals in an MRI scanner can also have electrical currents induced in them by the radio frequency pulses. For stents, this can lead to the stent shielding the lumen from the radio frequency excitation signal.

The medical devices of the present disclosure may be chosen from a stent, a guidewire, or an embolic protection device. The method comprises welding an above-mentioned radiopaque marker to an expandable or self-expanding section. The welding may comprise fusion welding. The expandable or self-expanding section may comprise a binary nickel-titanium alloy or ternary alloy of nickel and titanium. The ternary alloy comprises at least one ternary element chosen from platinum, palladium, gold and rhodium. In one exemplary embodiment, the ternary alloy may comprise 49 to 51 atomic percent titanium, 7 to 8 atomic percent platinum, the remainder nickel. Other exemplary embodiments are contemplated wherein the percentages of the alloy may vary as well as the ternary element.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Further modifications and improvements may additionally be made to the device and method disclosed herein without departing from the scope of the present invention. Accordingly, it is not intended that the invention be limited, except as by the appended claims.

What is claimed is:

1. A medical device, comprising:
an implantable body comprising a superelastic NiTi alloy;
a radiopaque marker, said radiopaque marker comprising a binary alloy of titanium and one binary element selected from platinum, palladium, rhodium, and gold, the titanium present in an amount ranging from 45 to 55 atomic percent and the balance of the binary alloy comprising said binary element; and
an autogenous weld joining the radiopaque marker and the implantable body together, wherein the implantable body, the radiopaque marker, and the autogenous weld exhibit a crystalline lattice that is substantially the same, allowing Ni of the Ni—Ti alloy and the binary element of the radiopaque marker to substitute for one another in one or more of the autogenous weld, in the implantable body adjacent to the autogenous weld, or in the radiopaque marker, and wherein the implantable body, the radiopaque marker, and the autogenous weld are substantially free of brittle intermetallic compounds such that the Ni—Ti superelastic alloy, the radiopaque marker, and the autogenous weld each maintain similar ductility.

2. The medical device of claim 1, wherein the titanium is present in an amount ranging from 49 to 51 atomic percent, with the balance comprising said binary element.

3. The medical device of claim 2, wherein the binary titanium alloy comprises equiatomic binary alloys chosen from Ti50Pt50, Ti50Pd50, Ti50Rh50, and Ti50Au50.

4. The medical device of claim 1, wherein said superelastic alloy comprises a binary nickel-titanium alloy or a ternary alloy of nickel and titanium.

5. The medical device of claim 4, wherein said ternary alloy of nickel and titanium comprises at least one ternary element chosen from platinum, palladium, gold and rhodium.

6. The medical device of claim 5, wherein the superelastic alloy is a ternary alloy of nickel, titanium, and platinum.

7. The medical device of claim 6, wherein the ternary alloy comprises 49 to 51 atomic percent titanium, 7 to 8 atomic percent platinum, the remainder comprising nickel.

8. The medical device of claim 1, wherein the implantable body is a stent, guidewire, or embolic protection device.

9. The medical device of claim 1, wherein said binary alloy is cold rollable to approximately 50 percent reduction in thickness without substantial edge cracking.

10. The medical device of claim 1, wherein the crystalline lattice is a B2 crystalline lattice.

11. A stent comprising:
an expandable or self-expanding NiTi alloy stent body; and
a radiopaque marker integrally attached to said expandable or self-expanding stent body by an autogenous weld, wherein said radiopaque marker comprises a binary alloy of titanium and one binary element selected from platinum, palladium, rhodium, and gold, the titanium present in an amount ranging from 45 to 55 atomic percent and the balance of the binary alloy comprising said binary element,
wherein the stent body, the radiopaque marker, and the autogenous weld exhibit substantially the same crystalline lattice, allowing Ni of the Ni—Ti alloy and the binary element of the radiopaque marker to substitute for one another in one or more of the autogenous weld, in the implantable body adjacent to the autogenous weld, or in the radiopaque marker such that the Ni—Ti superelastic alloy, the radiopaque marker, and the autogenous weld each maintain similar ductility, and
wherein the implantable body, the radiopaque marker, and the autogenous weld are substantially free of brittle intermetallic compounds such that the Ni—Ti superelastic alloy, the radiopaque marker, and the autogenous weld each maintain similar ductility.

12. The stent of claim 11, wherein the titanium is present in an amount ranging from 49 to 51 atomic percent, with the balance comprising said binary element.

13. The stent claim 12, wherein the binary titanium alloy comprises equiatomic binary alloys chosen from Ti50Pt50, Ti50Pd50, Ti50Rh50, and Ti50Au50.

14. The stent of claim 11, wherein said expandable or self-expanding stent body comprises a binary nickel-titanium alloy or a ternary alloy of nickel and titanium.

15. The stent of claim 14, wherein said ternary alloy of nickel and titanium comprises at least one ternary element chosen from platinum, palladium, gold and rhodium.

16. The stent of claim 14, wherein said ternary alloy of nickel and titanium comprises platinum.

17. The stent of claim 16, wherein the ternary alloy comprises 49 to 51 atomic percent titanium, 7 to 8 atomic percent platinum, the remainder comprising nickel.

18. A stent delivery system including the stent of claim 11, and further comprising a guidewire.

19. The stent delivery system of claim 18, wherein said guidewire has a radiopaque marker attached thereto by an autogenous weld.

20. The medical device of claim 11, wherein the stent body, the radiopaque marker, and the autogenous weld exhibit a B2 crystalline lattice.

21. The medical device of claim 11, wherein the autogenous weld includes at least a partial intermixture of metals from the implantable body and the radiopaque marker and wherein the each of the implantable body, the radiopaque marker, and the autogenous weld exhibit a B2 crystalline lattice.

22. A method of fabricating a medical device comprising a radiopaque marker, said method comprising:
autogenously welding to an expandable or self-expanding NiTi alloy section of the medical device, the radiopaque marker comprising a binary alloy of titanium and one binary element selected from platinum, palladium, rhodium, and gold, the titanium present in the binary alloy in an amount ranging from 45 to 55 atomic percent and the balance of the binary alloy comprising said binary element,
wherein each of the expandable or self-expanding section of the medical device, the radiopaque marker, and an autogenous weld coupling the expandable or self-expanding section of the medical device to the radiopaque marker exhibit a metallurgically compatible crystalline lattice, allowing Ni of the Ni—Ti alloy and the binary element of the radiopaque marker to substitute for one another in one or more of the autogenous weld, in the implantable body adjacent to the autogenous weld, or in the radiopaque marker, and
wherein each of the expandable or self-expanding section of the medical device, the radiopaque marker, and an autogenous weld are substantially free of brittle intermetallic compounds such that the Ni—Ti superelastic alloy, the radiopaque marker, and the autogenous weld each maintain similar ductility.

23. The method of claim 22, wherein the titanium is present in an amount ranging from 49 to 51 atomic percent, with the balance comprising said binary element.

24. The method of claim 23, wherein the binary titanium alloy comprises equiatomic binary alloys chosen from Ti50Pt50, Ti50Pd50, Ti50Rh50, and Ti50Au50.

25. The method of claim 22, wherein said autogenously welding comprises fusion welding.

26. The method of claim 22, wherein said expandable or self-expanding section comprises a binary of nickel-titanium or a ternary alloy of nickel and titanium.

27. The method of claim 26, wherein said ternary alloy of nickel and titanium comprises at least one ternary element chosen from platinum, palladium, gold and rhodium.

28. The method of claim 27, wherein said ternary alloy of nickel and titanium comprises platinum.

29. The method of claim 28, wherein the ternary alloy comprises 49 to 51 atomic percent titanium, 7 to 8 atomic percent platinum, the remainder comprising nickel.

30. The method of claim 22, wherein said medical device is chosen from a stent, guidewire, or embolic protection device.

31. The method of claim 22, wherein the metallurgically compatible crystalline lattice includes a B2 crystalline lattice.

* * * * *